US005720951A

United States Patent [19]

Baker

[11] Patent Number: 5,720,951
[45] Date of Patent: Feb. 24, 1998

[54] RODENTICIDE BAIT

[75] Inventor: Simon Dominic Baker, Finchampstead, United Kingdom

[73] Assignee: Zeneca Limited, London, England

[21] Appl. No.: 776,136

[22] PCT Filed: Jul. 11, 1995

[86] PCT No.: PCT/GB95/01629

§ 371 Date: Jan. 14, 1997

§ 102(e) Date: Jan. 14, 1997

[87] PCT Pub. No.: WO96/03037

PCT Pub. Date: Feb. 8, 1996

[30] Foreign Application Priority Data

Jul. 28, 1994 [GB] United Kingdom ............... 9415292

[51] Int. Cl.$^6$ ............... A01N 25/00; A01N 25/08; A01N 25/12; A01N 43/16

[52] U.S. Cl. ............... 424/84; 424/405; 424/408; 424/409; 424/410; 424/417; 424/489; 424/499; 424/50; 424/501; 424/502; 514/167; 514/432; 514/457; 514/681; 514/951; 426/1

[58] Field of Search ............... 424/84, 405, 408, 424/409, 410, 417, 489, 499, 500, 501, 502; 426/1; 514/167, 432, 457, 681, 951

[56] References Cited

U.S. PATENT DOCUMENTS

| 3,223,231 | 12/1965 | Connolly | 43/131 |
|---|---|---|---|
| 4,992,275 | 2/1991 | Lush | 424/408 |
| 5,044,113 | 9/1991 | Stack et al. | 43/131 |

FOREIGN PATENT DOCUMENTS

| 678097 | 9/1966 | Belgium . |
| 847653 | 4/1977 | Belgium . |
| 0198296 | 10/1986 | European Pat. Off. . |
| 0248929 | 12/1987 | European Pat. Off. . |
| 2197514 | 3/1974 | France . |
| 2260948 | 9/1975 | France . |
| 2659194 | 9/1991 | France . |
| 1929137 | 11/1969 | Germany . |
| 2317285 | 10/1974 | Germany . |
| 54-107516 | 8/1979 | Japan . |
| 348003 | 9/1960 | Switzerland . |

OTHER PUBLICATIONS

Shafi, M.M. et al., "Taste Enhancers Improve Poison Bait Acceptance in Field Rodents Damaging Wheat Crop," Tropical Pest Management, vol. 38, No. 2, pp. 214–217, 1992.

Shafi, M.M. et al., "Role of Some Taste Additives to Enhance Poison Bait Acceptance in Black Rat, Rattus Rattus L.," Tropical Pest Management, vol. 36, No. 4, pp. 371–374, 1990.

Shafi, M.M. et al., "Enhancement of Poison Bait Acceptance Through Taste Additives in Rattus Norvegicus," Joural of Stored Products Research, vol. 28, No. 4, 1992, pp. 239–243.

*Primary Examiner*—John Pak
*Attorney, Agent, or Firm*—Joel G. Ackerman

[57] ABSTRACT

A rodenticidal bait in the form of agglomerated granules comprising: a cereal base comprising a ground cereal; a rodenticide; and a water-soluble film-forming binder.

12 Claims, No Drawings

RODENTICIDE BAIT

This application is 371 of PCT/GB95/01629, filed on Jul. 11, 1995.

This invention relates to rodenticidal baits; that is to say, edible compositions which are attractive to rodents (especially rats and mice) and which contain a rodenticide.

Many types of bait are in commercial use and others have been proposed. They include grains; pellets usually prepared by extrusion or casting; wax blocks again usually prepared by extrusion or by casting, and wherein the edible material attractive to rodents is incorporated into the wax; and meal baits comprising cereals processed in various ways. Cereal based baits containing a rodenticide and a water-soluble film forming binder are described in, for example, DE-A-2317285, DE-A-1929137, CH-A-348003, FR-A-2260948 and FR-A-2659194. These baits are in the form of granules, for example pellets, generally produced by pressure compaction techniques. Such techniques include, for example, the use of a roll compactor (briquetting press) or a tabletting press. In addition, Belgian Patent 847,653 discloses rodenticidal baits consisting of a core of edible material coated with an external film which itself contains a rodenticide. None of these references suggests that the attraction of cereal based baits to rodents can be enhanced by using different size cereal particles in particular proportions.

According to the present invention there is provided a rodenticidal bait in the form of agglomerated granules having an open texture comprising (1) a cereal base in which from 2% to 10% of the cereal particles have a size in the range of equal to or greater than 500 μm up to less than or equal to 1000 μm, and from 70% to 90% of the cereal particles have a size in the range of equal to or less than 250 μm, (2) a rodenticide, and (3) a water-soluble film-forming binder.

Preferably, the rodenticidal bait contains a palatability-enhancing agent.

The rodenticide bait can contain further components, for example, a colouring agent, a preservative, or a substance to deter human consumption of the bait.

The size of agglomerated granules is preferably in the range of 0.20 mm to about 10 mm, more preferably about 0.25 mm to about 10 mm, even more preferably 0.25 mm to 5 mm.

Overall, the agglomerated granules are generally rounded in shape but with minor irregularities which provide attractive sites for gnawing by rodents.

The granules may be prepared by applying conventional granulating methods to a mixture of the components. The water soluble film-forming binder is included in the granulating process as an aqueous solution. As the wet granules formed in the process dry out, the film-forming binder stabilises the granules by binding together the particles of the components. The film-forming binder also causes individual granules to stick together to form agglomerates or lumps having an open texture because of gaps between the individual granules. (We would mention that to some extent the term "granulation" is used generically in the art as a convenient term to describe all the processes by which rodenticide baits have been prepared. However, the present invention relates to a novel rodenticide bait in the form of an agglomerated granule and processes for its preparation.)

This open texture may be more attractive to rodents than prior art baits. For example the open texture may be more attractive to rodents than solid block baits, such as pellets, since they are able to detach small portions from the granule agglomerate more easily than from a solid block or a pellet.

Indeed, the bait of the present invention which is rough and irregular can be contrasted with smooth and uniform prior art baits, particularly the pellet.

The agglomerated granules of the invention may also be more palatable to rodents than baits hitherto proposed, because the various non-palatable ingredients such as the dye and the rodenticide are distributed evenly throughout the granules and not confined for example to a film on the surface of the bait as in the bait disclosed in Belgian Patent 847,653.

As previously mentioned, a variety of processes may be used in preparing the bait into an agglomerated granule form; for example, mechanical agitation or fluidised bed granulation. Preferably the mechanical agitation method is used. Examples of machinery which can be employed in such a mechanical agitation method are: pan and rolling drum granulators, double arm mixers, ploughshare (Lodige) mixers, high shear granulators and ribbon blenders. While the operations may vary, depending on the particular process selected, a typical process would include the following steps:

(a) The dry powder components (e.g. ground cereals and optional palatability enhancers) are thoroughly blended together in a suitable mixer to form a premix. Typical blending times would be of the order of 1 to 10 minutes dependant on the machinery used. The mixer used for this operation could also be the means by which granulation is achieved (as assumed in this schematic process). (b) The rodenticide and the agent to deter human consumption of the bait, if appropriate, both preferably in the form of a liquid concentrate, are added to the premix described in (a) and the mixture is blended until homogenous. Typically, the concentrate would be sprayed onto the premix to aid the production of an even distribution. Typical, blending times would be of the order of 10 to 30 minutes.

(c) An aqueous solution of the film-forming binder, optionally containing a preservative, is sprayed onto the mixture described in (b) whilst the mixture is being blended. Alternatively, the film-forming binder solution may be mixed with the active ingredient concentrate and the resultant single liquid component sprayed onto the powder premix.

(d) The wet mass is mixed for the required length of time until granulation is achieved and the required particle size range is produced, typically this would be of the order of 1 to 5 minutes.

(e) The granule mass is then dried to a specified moisture level either in the granulator or in a separate apparatus (e.g. fluidised bed dryer). Typical moisture content would be in the range 5 to 15%. Drying times may vary and are dependant upon initial moisture content, drying temperature, air flow, etc. Typical drying temperature would be 80° to 100° C. and drying times would be of the order of 30 minutes.

(f) The granules are classified (e.g. by sieving) to the required particle size range. Typically, 0.20 mm, preferably 0.25 to 10 mm, as previously mentioned.

The agglomerated granules may be used to prepare other forms of bait. Thus, the wet granules prepared by the granulating process may be formed into blocks before drying. Alternatively, the granules, when dry, may be mixed with molten fat or wax and then moulded into blocks which are then allowed to cool and solidify. Such blocks may be prepared in a range of sizes, for example from 5 to 500 grams in weight.

Baits according to the invention have the following further advantages:

(1) They can withstand high levels of humidity without breaking down or becoming mouldy;

(2) They are highly acceptable to rodents;
(3) They are non-dusty in handling and application.

The cereals and other edible ingredients used in the bait are preferably of the highest grade available (ie human food grade). A variety of cereals may be used in the bait, for example wheat, barley, maize, sorghum, oats, rice, and millet. Other suitable cereals for rodenticide baits can be used in the present invention, and a skilled worker will know of such cereals. It will be appreciated that one or more cereals can be used in the present invention. A proportion of the cereal may be replaced if desired by a milled pulse (e.g. milled peas or beans).

In order to achieve the size of granule required, and to produce the open-textured agglomerated granules described above, it has been found desirable to use cereals of a particular particle size regime. The cereal is preferably not all reduced to the same particle size range (ie not all ground to flour, or all in the form of coarse particles such as cut-wheat grains). Preferably a mixture of particle size ranges is used, in which a minor proportion (less than 50%) of the cereal is in the form of relatively coarse particles (e.g. as in the larger particles of whole-ground wheat) while a major proportion is in the form of relatively fine particles (e.g. as in wheat flour).

Preferably the size of coarse particles is in the range of equal to or greater than about 500 µm but equal to or less than 1000 µm (1 mm). The preferred amount of coarse particles used in the agglomerated granules is in the range of from about 2% to about 10% by weight.

Preferably the size of the fine particles is equal to or less than 250 µm. The preferred amount of fine particles used in the agglomerated granules is in the range of about 70% to about 90%.

Obviously there are combinations of the two coarse and fine proportions that sum to less than 100%. Any missing proportion would be made up of intermediate particles, which are preferably are in the size range of 250 µm to 500 µm.

By way of example only, an analysis of the particle size range of two typical raw materials, namely medium whole ground wheat flour and fine ground oat flour, is given below:

| Sieve Aperature Size (µm) | Percentage Retained on Sieve * |
|---|---|
| Medium Whole Ground Flour | |
| 840 | 5 |
| 420 | 15 |
| 250 | 15 |
| 177 | 25 |
| 149 | 10 |
| Passing 149 | 30 |
| Fine Ground Oat Flour | |
| 500 | 2 |
| 300 | 10 |
| 212 | 10 |
| 150 | 20 |
| Passing 150 | 58 |

* Accuracy ± 5%

All sieve aperture sizes are quoted as micrometers (µm).

When using mixtures of cereals, if desired, one cereal may be used to provide the coarse particles and the other the fine particles. Examples of such mixtures include: finely ground maize with whole ground wheat; finely ground barley with whole ground wheat; whole ground wheat with finely ground oats; and finely ground wheat with whole ground barley.

Baits containing a mixture of two or more cereals may be more attractive to rodents than baits containing only a single cereal.

Preferably, the rodenticide bait includes a palatability-enhancing agent. The palatability-enhancing component of the bait may include, for example, a sweetener. The sweetener may be, for example, sugar (sucrose), optionally in the form of molasses. Other sweeteners may be used and examples of such sweeteners include acesulfame-K, alitame, aspartame, cyclamate, saccharin, sucralose, sorbitol, mannitol, xylitol, thaumatin, monellin, isomalt, and isomaltulose. Many of these materials have greater sweetening power than sucrose, and if used, they will be incorporated at a concentration appropriate to their sweetening power.

Other palatability-enhancing agents include animal and vegetable oils for example fish oil, and maize, peanut, and soyabean oil, and dried yeast.

The concentration of the palatability-enhancing agent in the final bait composition will vary depending on its identity but will typically be in the range from about 1 to about 5 percent by weight. The amount to be used will be known by a person skilled in the art, or can be determined by routine experimentation.

The bait according to the invention may contain one or more rodenticides. The rodenticide may be any known or developed rodenticide. Examples of commercially available rodenticides include brodifacoum; difethialone; flocoumafen; bromadiolone; warfarin; cholecalciferol; chlorphacinone; diphenacoum; coumatetratyl; diphacinone and phenindione.

The concentration of the rodenticide in the final bait may vary somewhat according to the particular active ingredient used, but will usually be in the range from about 5 to about 550 parts per million (ppm), preferably in the range of about 10 to about 500 ppm, more preferably about 10 to about 250 ppm, and even more preferably in the range of from about 10 to about 100 ppm. However, again an appropriate amount of rodenticide will be known by a skilled worker or readily determinable by routine experimentation.

The water-soluble film-forming binder is used in the bait according to the invention to help agglomerate the cereal base and the other ingredients into granules, and gives the granules their strength and resistance to environmental deterioration. Once the aqueous solution of binder has evaporated from the granules, the film of binder which is left is required to adhere strongly to hydrophilic surfaces, to be flexible with high mechanical strength, non-hygroscopic and non-tacky at high humidity, bland in taste, and not repellent to rodents. Examples of binders include: cellulose ethers, for example methyl cellulose, ethyl cellulose, methyl hydroxyethyl cellulose, methyl hydroxypropyl cellulose, hydroxyethyl cellulose, and hydroxypropyl cellulose; starch from various sources (e.g. potato or wheat); polyvinyl alcohol; polyvinyl pyrrolidone; guar gum; carrageenan; gelatin; xanthan gum; acacia gum; locust bean gum; karaya gum; tragacanth; pectin; and polyacrylates. Hydroxypropyl cellulose is a preferred binder.

Although the binders as supplied commercially (usually in the form of a powder) are water soluble, they do not in general dissolve readily in water but require mechanical agitation over a period of time to bring them into solution. When the solution of the binder evaporates from the rodent bait, the film of binder left on the surface of the particles cures and becomes more resistant to dissolution in water, and hence is able to increase the physical structure of the bait against degradation in conditions of high humidity.

The concentration of the binder in the bait may vary depending on for example the particular binder chosen for use, but in general will be from about 1 to about 10 percent by weight, and usually from about 1 to about 5 percent.

Again, an appropriate amount of the binder can be readily determined using routine experimentation.

The bait according to the invention may also contain a preservative to reduce or prevent degradation of the bait by microorganisms, or an anti-oxidant to reduce the tendency of the bait to degrade by oxidation. Examples of preservatives include sorbic acid and its salts (e.g. the potassium salt), propionic acid, and benzisothiazolones. The concentration of the preservative may vary depending for example on the identity of the preservative used, but in general may be from about 0.05 to about 0.2 percent by weight. Examples of anti-oxidants include propyl gallate and butylated hydroxyanisole. The concentration of the anti-oxidant will usually be in the range from about 0.05 to about 0.1 percent by weight.

The bait according to the invention may also contain an agent to deter human consumption of the bait, for example the bittering agent denatonium benzoate or another salt of the denatonium cation. Preferably this substance is used at a concentration of about 0.001 percent by weight.

The bait may also contain a colouring agent comprising a dye or pigment.

The bait may also contain an additive to increase its resistance to moisture, for example a wax. Examples of waxes include carnauba wax; waxes used in the food industry, (e.g. beeswax); and refined waxes used in the chemical industry (e.g. purified paraffin wax). The concentration of the wax will usually be in the range from about 1 to about 3 percent by weight.

Again an appropriate amount of such optionally components will either be known by a skilled worker or can be determined using routine experimentation.

The granules may be used both inside buildings and other structures, or outdoors. The granules may be placed in suitable locations by transferring them from a bulk container. They may also be used in place packs (ie packs containing a pre-measured dose) or in bait stations. They may also be used in a mouse box or tube or may be dispensed from a device designed to deliver a pre-measured dose.

Further preferred features and embodiment of the present invention will now be illustrated by the following non-limiting Examples, in which, unless stated otherwise, all parts are by weight. The brodifacoum liquid concentrate referred to in the Examples has the following composition:

| Ingredient | Concentration (percentage by weight) |
|---|---|
| Technical brodifacoum | x* |
| Triethanolamine | 6 |
| Polyethylene Glycol 200 | 4-x |
| Durazol Blue BG | 10 |
| "Bitrex" powder | 0.1 |
| Propylene glycol | to 100 |

*where x gives 0.5 percent by weight active brodifacoum.
Durazol Blue BG is a Trade Mark for a composition containing a triphenodioxazine dye, and Bitrex is a Trade Mark for a bittering agent comprising a salt of the denatonium cation.

EXAMPLE 1

This Example illustrates the composition of a rodent bait according to the invention.

| Ingredient | | % w/w |
|---|---|---|
| Brodifacoum liquid concentrate | (toxicant) | x |
| Icing sugar | (palatability enhancer) | 2.0 |
| Hydroxypropyl cellulose | (film former) | 2.0 |
| Proxel GXL | (preservative) | 0.15 |
| Whole ground wheat | (palatable base) | to 100 | where x gives 0.005% w/w brodifacoum and 0.001% w/w "Bitrex"
Proxel GXL is a Trade Mark for a preservative comprising 1,2-benzisothiazolin-3-one.

EXAMPLE 2

This Example illustrates the composition of a rodent bait according to the invention.

| Ingredient | | % w/w |
|---|---|---|
| Brodifacoum liquid concentrate | (toxicant) | x |
| Icing sugar | | 2.0 |
| Vegetable oil | (palatability agent) | 2.0 |
| Hydroxypropyl cellulose | (film former) | 2.0 |
| Proxel GXL | (preservative) | 0.15 |
| Whole ground wheat | (palatable base) | to 100 | where x gives 0.005% w/w brodifacoum and 0.001% w/w "Bitrex"

EXAMPLE 3

This Example illustrates the composition of a rodent bait according to the invention.

| Ingredient | | % w/w |
|---|---|---|
| Brodifacoum liquid concentrate | | x |
| Icing sugar | | 2.0 |
| Hydroxypropyl cellulose | | 2.0 |
| Proxel GXL | (preservative) | 0.15 |
| Butylated hydroxyanisole | (anti oxidant) | 0.1 |
| Citric acid | (anti oxidant) | 0.1 |
| Whole ground wheat | (palatable base) | to 100 | where x gives 0.005% w/w brodifacoum and 0.001% w/w "Bitrex"

EXAMPLE 4

This Example illustrates the composition of a rodent bait according to the invention.

| Ingredient | | % w/w |
|---|---|---|
| Brodifacoum liquid concentrate | | x |
| Icing sugar | | 2.0 |
| Hydroxypropyl cellulose | | 2.0 |
| Potassium sorbate | (preservative) | 0.3 |
| Carnauba wax | (waterproofing agent) | 2.0 |
| Whole ground wheat | | to 100 | where x gives 0.005% w/w brodifacoum and 0.001% w/w "Bitrex"

EXAMPLE 5

This Example illustrates the composition of a rodent bait according to the invention.

| Ingredient | % w/w |
| --- | --- |
| Brodifacoum liquid concentrate | x |
| Molasses | 5.0 |
| Hydroxypropyl cellulose | 2.0 |
| Dye | 0.1 |
| Proxel GXL | 0.15 |
| Oatflour (finely ground cereal) | 37 |
| Whole ground wheat (coarse ground cereal) | to 100 | where x gives 0.005% w/w brodifacoum and 0.001% w/w "Bitrex"

EXAMPLE 6

This Example illustrates the composition of a rodent bait according to the invention.

| Ingredient | % w/w |
| --- | --- |
| Brodifacoum liquid concentrate | x |
| Icing sugar | 5.0 |
| Dye | 0.1 |
| Hydroxypropyl cellulose | 2.0 |
| Proxel GXL | 0.15 |
| Oatflour (finely ground cereal - palatable base | 37 |
| Whole ground wheat (coarse ground cereal, material mixture) | to 100 | where x gives 0.005% w/w brodifacoum and 0.001% w/w "Bitrex"

EXAMPLE 7

The Example illustrates the composition of a rodent bait according to the present invention.

| Ingredient | % w/w |
| --- | --- |
| Brodifacoum liquid concentrate | x |
| Saccharin | 0.1 |
| Dye | 0.1 |
| Hydroxypropyl cellulose | 2.0 |
| Proxel GXL | 0.15 |
| Oat flour (finely ground cereal) | 37 |
| Whole ground wheat (coarse ground cereal) | to 100 | where x gives 0.005% w/w brodifacoum and 0.001% w/w "Bitrex"

EXAMPLE 8

This Examples illustrates that the rodenticide bait of the present invention provides good rodent control.

The test species were Welsh Farmstead *Rattus norvegicus* and *Mus musculus*. Five males and five females were used per test, and the animals were individually caged. The animals were conditioned on laboratory diet for four days prior to the test. Pre and post trial the animals were fed with control bait which did not contain the active ingredient, which in these trials was brodifacoum. The quantity of food eaten pre and post trial provides an indication of the population of the rodents, and can be used to determine % control. During the test with a brodifacoum agglomerated granule of the present invention the animals were given the choice between two test diets for three days. Water was available ad lib through the trial. The quantity of each diet consumed was assessed by weight daily, and at the end of the trial, the quantity eaten summed for 10 animals, two sexes, over the three days and expressed as a percentage of total food consumption.

| Species | Trial | Consus bait consumption (g) Pre-trial | Post-trial | % Control |
| --- | --- | --- | --- | --- |
| Rattus | 1 | 718 | 0 | 100% |
| Rattus | 2 | 3093 | 170 | 94.5% |
| Mus | 1 | 146 | 6 | 95.9% |
| Mus | 2 | 98 | 0 | 100% |

EXAMPLE 9

This Example illustrates the preference of rats and mice for an agglomerated granule of the present invention. The acceptance of rats and mice for an agglomerated granule of the present invention, comprising 0.1% bromadiolone concentrate, 0.001% w/w Bitrex, sweetener, Proxel GXL, oatflour and fine wheat, against the unformulated pre-mix of the components (powder) was tested. Ten animals were used in each test.

| Bromadiolone (50 ppm) | | |
| --- | --- | --- |
| Rats | 88.4% acceptance for the granule | (11.6% powder) |
| Mice | 61.5% acceptance for the granule | (38.5% powder) |

EXAMPLE 10

This Example illustrates the preference of rats and mice for an agglomerated granule of the present invention. The acceptance of rats and mice for an agglomerated granule of the present invention against a commercially available wheat based pellet was tested. Both formulations contained the same active ingredient, brodifacoum 50 ppm, together with 10 ppm Bitrex.

| Rats | 64.7% acceptance for the granule | (35.3% pellet) |
| --- | --- | --- |
| Mice | 69.6% acceptance for the granule | (30.4% pellet) |

I claim:

1. A rodenticide bait in the form of agglomerated granules having an open texture that is rough and irregular, wherein each agglomerated granule is in the size range of from 0.2 mm to 10 mm, comprising:

a cereal base in which from 2% to 10% by weight of the cereal particles have a size in the range of equal to or greater than 500 µm up to less than or equal to 1000 µm and from 70% to 90% by weight of the cereal particles have a size in the range of equal to or less than 250 µm;

a rodenticide; and a water-soluble film-forming binder.

2. A rodenticide bait according to claim 1, further comprising a palatability-enhancing agent.

3. A rodenticide bait according to claim 2, wherein the palatability-enhancing agent is a sweetener, an animal oil, a vegetable oil, or yeast.

4. A rodenticide bait according to claim 2, wherein the rodenticide bait contains from 1% to 5% by weight of the palatability-enhancing agent.

5. A rodenticide bait according to claim 1, wherein each agglomerated granule is in the size range of from 0.25 mm to 5 mm.

6. A rodenticide bait according to claim 1, further comprising a colouring agent, a preservative, or a substance to deter human consumption of the bait.

7. A rodenticide bait according to claim 1, in which the water-soluble film-forming binder is a cellulose ether, a starch, polyvinyl alcohol, polyvinyl pyrrolidone, carrageenan, gelatin, a gum, tragacanth, pectin, or a polyacrylate.

8. A rodenticide bait according to claim 1, wherein the rodenticide bait contains from 1% to 10% by weight of the water-soluble film-forming binder.

9. A rodenticide bait according to claim 1, wherein rodenticide is brodifacoum, difethialone, flocoumafen, bromadiolone, warfarin, cholecalciferol, chlorphacinone, diphenacoum, coumatetralyl, diphacinone or phenindione.

10. A rodenticide bait according to claim 1, wherein the rodenticide bait contains from 5 ppm to 550 ppm by weight of the rodenticide.

11. A rodenticide bait according to claim 1, wherein the ground cereal is wheat, barley, maize, sorghum, oats, rice or millet.

12. A method for the production of a rodenticide bait according to claim 1, comprising mixing by mechanical agitation or by fluidised bed granulation a cereal base in which from 2% to 10% by weight of the cereal particles have a size in the range of equal to or greater than about 500 μm up to less than or equal to 1000 μm and from 70% to 90% by weight of the cereal particles have a size in the range of equal to or less than about 250 μm; a rodenticide; and a water-soluble film-forming binder; and granulating the mixture to granules having an open texture that is rough and irregular, wherein each agglomerated granule is in the size range of from 0.2 mm to 10 mm.

* * * * *